United States Patent [19]
Langer et al.

[11] Patent Number: 6,054,619
[45] Date of Patent: Apr. 25, 2000

[54] PROCESS FOR PREPARING CYCLOALIPHATIC AMINES

[75] Inventors: Reinhard Langer, Tönisvorst; Gerd-Michael Petruck, Erkrath, both of Germany

[73] Assignee: Bayer Aktiengesellschaft, Leverkusen, Germany

[21] Appl. No.: 09/332,327

[22] Filed: Jun. 14, 1999

[30] Foreign Application Priority Data

Jun. 19, 1998 [DE] Germany .............................. 198 27 282

[51] Int. Cl.$^7$ .......................... C07C 209/00; B01J 23/00
[52] U.S. Cl. ........................... 564/450; 564/451; 502/313
[58] Field of Search .................................... 564/450, 451; 502/313

[56] References Cited

U.S. PATENT DOCUMENTS

| | | |
|---|---|---|
| 3,636,108 | 1/1972 | Brake . |
| 4,049,584 | 9/1977 | Weissel . |
| 4,960,941 | 10/1990 | Vedage et al. . |
| 5,023,226 | 6/1991 | Immel et al. . |
| 5,360,934 | 11/1994 | Vedage et al. . |
| 5,773,657 | 6/1998 | Rutter et al. . |

FOREIGN PATENT DOCUMENTS

| | | |
|---|---|---|
| 0 560 127 | 9/1993 | European Pat. Off. . |
| 1530477 | 5/1968 | France . |

OTHER PUBLICATIONS

P.N. Rylander, Hydrogenation Methods, Academic Press, (month unavailable) 1985, pp. 123–133, Hydrogenation of anilines, Phenols, and Derivatives.

Chemical Abstract, vol. 71, Sep. 29–Oct. 29, (1969) Abstract No. 60838e, Ugine Kuhlmann, FR 1,530,477, Jun. 28, 1968, Cyclohexylamine & Dicyclohexlamine.

J. Chem. Soc., Chem. Commun. (month unavailablel) 1990, Venkataraman Vishwanathan & Sankarasubbier Narayanan, A Direct Correclation between Dispersion, Metal Area and Vapor Phase Hydrogenation of Aniline; a First Report, pp. 78–80.

R.N. Rylander, Catalytic Hydrogenation over Platinum Metals, Academic Press, (month unavailable) 1967, pp. 331–363, Phenols and Phenyl Ethers.

*Primary Examiner*—Paul J. Killos
*Attorney, Agent, or Firm*—Joseph C. Gil; Diderico van Eyl

[57] ABSTRACT

The present invention relates to a low-pressure process for hydrogenating aromatic amines to give the corresponding cycloaliphatic amines in the presence of rhodium catalysts.

12 Claims, No Drawings

PROCESS FOR PREPARING CYCLOALIPHATIC AMINES

BACKGROUND OF THE INVENTION

The present invention relates to a low-pressure process for hydrogenating aromatic amines into the corresponding cycloaliphatic amines in the presence of rhodium catalysts which, if desired, are modified with a noble metal selected from among iridium (Ir), ruthenium (Ru), osmium (Os), palladium (Pd) or platinum (Pt) or a mixture of these metals on supports modified with oxides of the metals chromium (Cr), molybdenum (Mo), tungsten (W), manganese (Mn), or rhenium (Re) or a mixture of these oxides.

FR 1,530,477 describes a low-pressure process in which aniline is reacted in a stream of hydrogen containing large amounts of ammonia over supported Pd catalysts at temperatures of from 175° C. to 190° C. The product contains large amounts of dicyclohexylamine.

EP-A 0,560,127 describes a low-pressure process in which aniline is reacted over base-modified supported Ru-Pd catalysts. The catalysts allow only a very small throughput, have to be operated in the presence of large amounts of ammonia and in spite of this produce cyclohexylamine with a maximum selectivity of only 89%.

U.S. Pat. No. 5,360,934 discloses a process for the hydrogenation of aromatic amines using a supported rhodium catalyst. The support consists of κ-, θ- or δ-$Al_2O_3$. U.S. Pat. No. 4,960,941 also discloses a process for the hydrogenation of aromatic amines using a supported rhodium catalysts. The support consists of $TiO_2$. Both processes teach a pressure hydrogenation in the liquid phase.

U.S. Pat. No. 5,773,657 discloses the hydrogenation of aromatic compounds in which at least one amino group is bonded to an aromatic nucleus. The process teaches utilization of ruthenium catalysts, working in the liquid phase and pressures above 50 bar, preferably from 150 to 300 bar.

U.S. Pat. No. 5,023,226 describes a high-pressure process for hydrogenating aromatic amines in the presence of ruthenium catalysts which are modified with palladium and/or platinum on a support treated with chromium and manganese from the group consisting of $Al_2O_3$ and aluminum spinel.

A process which, at low pressures, selectively converts aromatic airlines into cycloaliphatic amines over a fixed catalyst bed and in which the catalyst is stable and allows throughputs of more than 0.1 kg/l×h of aromatic amine, for example aniline, per liter of catalyst and hour and in which no or only little ammonia has to be circulated is unknown.

There is also speculation in the literature suggesting that Rh catalysts should be suitable for low-pressure hydrogenations of anilines (P.N. Rylander, Catalytie Hydrogenation over Platinum Metals, Academic Press 1967 p. 331–363; P.N. Rylander, Hydrogenation Methods, Academic Press 1985, p.123–133).

A prejudice against the development of an Rh catalyst for the production of cyclohexylamines at low pressure arose from a study published a few years ago on the gas-phase hydrogenation of aniline over Rh on γ-$Al_2O_3$: at 1 atm and 200° C., increasing conversions were obtained with increasing Rh content of the catalyst, but the cyclohexylamine selectivity was, at about 20%, very low regardless of the conversion. The dicyclohexylamine selectivity even dropped with increasing Rh content and thus with increasing conversion from 40 to 20%, so that mostly undesired products were obtained. (V. Vishwanathan, S. Narayanan, J. Chem. Soc., Chem. Commun., 1990, 78–80). The publication suggests that rhodium catalysts are unsuitable for industrial hydrogenations of anilines to cyclohexylamines at low pressures in the gas phase.

It is an object of the present invention to find a selective low-pressure process for hydrogenating aromatic amines, for example anilines, to give cycloaliphatic amines (for example cyclohexylamines) which allows good throughputs.

It has surprisingly been found that catalysts containing Rh on specifically treated supports are potent catalysts for the realization of a process for the low-pressure hydrogenation of aromatic amines.

SUMMARY OF THE INVENTION

The invention relates to a process for hydrogenating aromatic amines to give cycloaliphatic amines at pressures of from 0.5 to 40 bar over supported noble metal catalysts which have been treated with bases, characterized in that the support has been laden with salts of Cr, Mo, W, Mn or Re or a mixture of these salts and in that the resulting support has been activated with Rh as noble metal and, if desired, Ir, Ru, Os, Pd and/or Pt as additional noble metal component. The invention also relates to the catalyst and a method for making the catalyst.

DETAILED DESCRIPTION OF THE INVENTION

Suitable starting compounds for the process of the invention are aromatic amines as are described, for example, in DE-AS (German Published Specification) 2,509,894 and U.S. Pat. No. 3,636,108. Preference is given to aniline, $C_1$–$C_6$-alkylanilines alkylated either on the ring or on the nitrogen, $C_1$–$C_6$-alkylated diaminobenzenes, aminonaphthalenes and $C_1$–$C_3$-alkylated aminonaphthalenes, diaminonaphthalenes and diamino-diphenyl-$C_1$–$C_3$-alkanes. Examples which may be mentioned are aniline, N-methylaniline, N-ethylaniline, N,N-dimethylaniline, N,N-diethylaniline, N-ethyltoluidine, N-cyclohexyl-aniline, N-cyclohexylideneaniline, o-, m-, p-toluidine, 2,4-, 2,6-, 2,3-diaminotoluene, diphenylamine, 1- and 2-aminonaphthalene, 1,4-, 1,5-, 2,5-, 2,6-, 2,7-diaminonaphthalene and the isomeric diaminophenylmethanes. Preferred examples are aniline, N-methylaniline, N-ethylaniline, N,N-dimethylaniline, N,N-diethylaniline, N-cyclohexylaniline, N-cyclohexyl-ideneaniline, o-, m-, p-toluidine, 2,4-, 2,6-, 2,3-diaminotoluene, diphenylamine. Particularly preferred examples are aniline, 2,4- and 2,6-diaminotoluene. The process of the invention is very particularly preferably used for hydrogenating aniline.

The supported noble metal catalysts for the process of the invention comprise a support which has been laden with a salt of the metals Cr, Mo, W, Mn or Re or a mixture of these salts. In addition, the supported noble metal catalysts contain Rh as noble metal and, if desired, an additional noble metal component selected from among Ir, Ru, Os, Pd and/or Pt.

Supports for the supported noble metal catalysts in the process of the invention are aluminas, $Al_2O_3$ in its various modifications (α,κ,η,γ), also supports otherwise customary for noble metals, e.g. $TiO_2$, kieselguhr, silica gel, $BaCO_3$, $CaCO_3$, ZnO, MgO, pumice, $ZrO_2$, activated carbon and naturally the oxides or hydrated oxides of Cr, Mo, W, Mn and/or Re. Preferred supports are $TiO_2$, $BaCO_3$, MgO, particularly preferably γ-$Al_2O_3$ or the oxides or hydrated oxides of Cr, Mo, W, Mn and/or Re, very particularly preferably γ-$Al_2O_3$.

The support can be used as powder or in pelletized form as spheres or as extrudates such as rings, wagon wheels, etc.; it is also possible to use shaped bodies such as honeycombs or cross-channel structures.

Preference is given to using a support having a large BET surface area. The BET surface area should be above 50 m$^2$/g, preferably from 100 to 500 m$^2$/g, particularly preferably from 200 to 400 m$^2$/g.

If the support contains oxides or hydrated oxides of metals selected from among Cr, Mo, W, Mn or Re or a mixture of such oxides or hydrated oxides, it may be possible to omit the modification described below of the support prior to application of the noble metal components.

If a support free of Cr, Mo, W, Mn or Re is used, this first has to be laden with one or more of these components. This can be achieved, for example, by impregnating or spraying the support with suitable salts of these elements. Drying and then heating at temperatures of from about 200 to 450° C. converts the salts which have been applied into compounds which adhere to the support. However, the application of the compounds of Cr, Mo, W, Mn and/or Re can also be achieved by coprecipitation of oxide/hydroxide mixtures onto the impregnated support using alkali metal, alkaline earth metal or ammonium hydroxides and, if desired, subsequent washing out of soluble components using water.

Particular preference is given to uniform precipitation by slow release of the base by hydrolysis of a less basic precursor, for which ureas and urethanes are particularly suitable; urea is especially suitable.

The support which has been pretreated in this way is dried and then heated for, for example, from 10 minutes to 10 hours at from 200 to 450° C., preferably from 250 to 430° C., where the temperature can also be increased in steps within this range.

Suitable salts of Cr, Mo, W, Mn and Re are, for example, the acetates, nitrates, halides or sulphates. Likewise suitable are the water-soluble oxides of the higher oxidation states, particularly the ammonium salts of Cr, Mo, W, Mn and Re oxides. Preference is given to using supports which have been pretreated with Cr and Mn salts.

After any washing out of soluble compounds and drying and heating the support modified with Cr, Mo, W, Mn and/or Re, the support is ready for application of the other active substances.

The other active substances are Rh and, if desired, a noble metal selected from among Ir, Ru, Os, Pd and/or Pt, alkali metal hydroxide or alkaline earth metal hydroxide and, if desired, alkali metal sulphate or alkaline earth metal sulphate. The noble metals are applied in the form of solutions of their salts, for example in water. Suitable salts are, for example, the halides, preferably the chlorides, acetates, nitrates and acetylacetonates. A suitable alkali metal hydroxide is, for example, NaOH or KOH; an example of a suitable alkaline earth metal hydroxide is Mg(OH)$_2$.

An example of a sulphate component is K$_2$SO$_4$. The compounds can be applied individually or together by impregnation or spraying. Drying is carried out between each impregnation step.

The alkali metal hydroxide or alkaline earth metal hydroxide can be applied prior to or after application of the nobel metals.

The order of application is preferably first Rh, then, if desired, the noble metals for modification, followed by the alkali metal hydroxide and, if desired, the alkali metal sulphate and, if desired, a further impregnation with base.

A reduction with, for example, hydrogen or another reducing agent is preferably carried out after each impregnation with noble metal; in any case, a reduction with, for example, hydrogen at temperatures of from 80 to 350° C. is carried out at the end of the last drying step.

The finished supported noble metal catalyst contains from 0.1 to 10% by weight, preferably from 0.3 to 3% by weight, of noble metal of which from 100 to 30%, preferably from 100 to 70%, is Rh; the remaining noble metal consists of Ir, Ru, Os, Pd and/or Pt. The catalyst additionally contains from 0.05 to 5% by weight of Cr, Mo, W, Mn and/or Re, preferably Cr and Mn, plus from 0.05 to 15% by weight of alkali metal or alkaline earth metal ions and, if desired, from 0.05 to 3% by weight of sulphur in the form of compounds.

In the process of the invention, preference is given to using a suitable supported noble metal catalyst in pelletized form as fixed beds. The beds can be adiabatic or be thermostatted by use of tube bundles through or around which heat-transfer media flow. Likewise advantageous is a combination of thermostatted and adiabatic beds or a sequence of adiabatic reactors with coolers located between them. The design of suitable reactors for such beds is prior art and known to those skilled in the art.

The reaction can be carried out by heating aromatic amine and hydrogen, if desired together with compounds to be recycled, e.g. hydrogen, ammonia end dicyclohexylamine, passing the heated mixture over the catalyst, condensing part of the condensable compounds by cooling and discharging this part together with any liquid already present, bleeding off part of the remaining gas stream to remove inert compounds from the system and returning the remainder, via compression, to the reaction. A gaseous starting material mixture is fed to the reactor.

The process of the invention is carried out at temperatures of fronr 50° C. to 300° C., preferably from 100° C. to 250° C., particularly preferably from 140° C. to 200° C.

The reaction is carried out in a pressure range from 0.5 to 40 bar, preferably from 0.7 to 15 bar, particularly preferably from 0.9 to 8 bar.

The aromatic amine to be reacted can be reacted with hydrogen in a molar ratio of from 1:500 to 1:5, preferably from 1:200 to 1:10, particularly preferably from 1:150 to 1:40.

Small amounts of ammonia can be passed over the catalyst together with the aromatic amines and the hydrogen. Ammonia significantly reduces the reaction rate and improves the cyclohexylamine selectivity only relatively slightly.

The space velocity over the catalysts in the process of the invention can be from 0.05 to 5 kg, preferably from 0.2 to 2 kg, of aromatic amine per liter of catalyst and hour.

When using aniline, the selectivities in respect of cyclohexylamine in the process of the invention are significantly above 97%, generally above 99%.

The process of the invention makes it possible to convert aromatic amines, in particular anilines, with high selectivity into cycloaliphatic amines, in particular cyclohexylamines, in relatively inexpensive low-pressure apparatus.

The invention is further illustrated but is not intended to be limited by the following examples in which all parts and percentages are by weight unless otherwise specified.

EXAMPLES

Example 1 (Catalyst preparation)

1 l of γ-Al$_2$O$_3$ from Rhone-Poulenc (SPH 501, spheres, diam.=4–6 mm, BET surface area about 350 m$^2$/g) were impregnated with 320 ml of a solution of 30.1 g of $MnSO_4 \cdot xH_2O$, 22.3 g of $(NH_4)_2Cr_2O_7$ and 164 g of urea. The impregnated support was kept in motion in a saturated steam atmosphere for 1 hour at 90° C. It was then washed twice with 160 ml each time of water to remove soluble compounds. The support obtained in this way was dried and subsequently heated at 300° C. for 30 minutes in a rotating drum.

20.3 g of $RhCl_3$ in 360 ml of water were applied by impregnation and the catalyst precursor was subsequently dried at 110° C.

320 ml of a solution of 24 g of NaOH and 24 g of $K_2SO_4$ in water were then applied, the catalyst precursor was dried and impregnated once again with 50 g of NaOH in 320 ml of water.

The catalyst was dried and activated in a stream of hydrogen for 3.5 hours at 160° C.

The finished catalyst contains 8 g of Rh, 9.2 g of Cr, 9.8 g of Mn, 74 g of NaOH and 24 g of $K_2SO_4$ per liter.

Example 2 (Influence of temperature at atmospheric pressure)

An oil-thermostatted reaction tube having an internal diameter of 2.5 cm was charged with 120 ml of catalyst from Example 1. The length of the bed was about 24 cm. The catalyst was activated in a stream of hydrogen for 3.5 hours at 160° C., and the reaction conditions indicated in Table 1 were then set and maintained in succession.

TABLE 1

Variations of the reaction temp.: Space velocity.: 0.2–0.3 kg/l × h, $H_2/ANI$ = 80/1 mol/mol. Cat.: 120 ml of catalyst from Example 1.

| Temp. ° C. | ANI % | Bz % | CA % | CHA % | DCA % | UC % | Select. % |
|---|---|---|---|---|---|---|---|
| 226 | 25 | 1.7 | 0.1 | 70 | 0.3 | 1.7 | 93.3 |
| 200 | 4 | 1.8 | 0.1 | 91 | 1.9 | 1.8 | 94.8 |
| 180 | 1.3 | 0.4 | 0 | 96 | 1.8 | 0.4 | 97.3 |
| 160 | 0.2 | 0 | 0 | 97 | 2.6 | 0 | 97.2 |

Table 1 shows the composition of the liquid phase after cooling the product stream to about 10° C. It can be seen that the conversion achieved at atmospheric pressure in the temperature range studied increases significantly as the temperature decreases. The conversions achieved are obviously determined by thermodynamic criteria. ANI = aniline; Bz = benzene; CA = cyclohexane; CHA = cyclohexylamine; DCA = dicyclohexylamine; UC = unknown components, Select. = selectivity.

Example 3 (Influence of the excess of hydrogen at atmospheric pressunre)

In the test set-up as described in Example 2, the hydrogen/aniline ratio in the feed stream was varied. Table 2 again shows the composition of the condensed phase. It can be seen that the selectivity in respect of cyclohexylamine drops slightly as the amount of hydrogen decreases.

TABLE 2

Aniline hydrogenation, oil temperature = 164° C., 1 atm, $H_2$ stream. Cat.: 120 ml of catalyst from Example 1.

| $H_2$/aniline mol/mol | Space velocity kg/l × h | ANI % | CHA % | DCA % | Anone + Anol % | LB % | UC % |
|---|---|---|---|---|---|---|---|
| 40 | 0.22 | 0 | 97.8 | 1.9 | 0.24 | 0.06 | 0.03 |
| 40 | 0.22 | 0 | 98.3 | 1.5 | 0.13 | 0.09 | 0.02 |

TABLE 2-continued

Aniline hydrogenation, oil temperature = 164° C., 1 atm, $H_2$ stream. Cat.: 120 ml of catalyst from Example 1.

| $H_2$/aniline mol/mol | Space velocity kg/l × h | ANI % | CHA % | DCA % | Anone + Anol % | LB % | UC % |
|---|---|---|---|---|---|---|---|
| 22 | 0.22 | 0 | 96.8 | 2.8 | 0.22 | 0.21 | 0.08 |
| 10 | 0.22 | 0 | 94.6 | 4.6 | 0.33 | 0.35 | 0.05 |
| 40 | 0.22 | 0 | 98.3 | 1.4 | 0.24 | 0.08 | 0.06 |

LB = Low boilers, for example compounds which appear before cyclohexylamine in the analysis by gas chromatography
Anone + Anol = Cyclohexanone + Cyclohexanol

Example 4 (Influence of the space velocity under atmospheric pressure)

TABLE 3

Aniline hydrogenation, oil temperature = 164° C., 1 atm, $H_2$ stream. Cat.: 120 ml of catalyst from Example 1.

| $H_2$/aniline mol/mol | Space velocity kg/l × h | ANI % | CHA % | DCA % | Anone + Anol % | LB % | UC % |
|---|---|---|---|---|---|---|---|
| 22 | 0.22 | 0 | 96.8 | 2.8 | 0.22 | 0.21 | 0.08 |
| 10 | 0.22 | 0 | 94.6 | 4.6 | 0.33 | 0.35 | 0.05 |
| 40 | 0.22 | 0 | 98.3 | 1.4 | 0.24 | 0.08 | 0.06 |
| 20 | 0.44 | 2.1 | 96.0 | 1.6 | 0.11 | 0.19 | 0.03 |
| 11 | 0.44 | 4.2 | 92.7 | 2.7 | 0.08 | 0.27 | 0.05 |
| 20 | 0.44 | 3.5 | 94.5 | 1.7 | 0.14 | 0.16 | 0.05 |

Table 3 shows the influence of the space velocity on conversion and selectivity. If the space velocity is doubled from 0.22 to 0.44 kg/l × h at atmospheric pressure, then admittedly the aniline is no longer converted completely but the selectivity rises slightly.

Example 5 (Operating life test)

Table 4 shows that the catalyst from Example 1 and 2 hydrogenates aniline to form cyclohexylamine with high conversion and high selectivity at atmospheric pressure for long periods of time.

TABLE 4

Aniline hydrogenation, oil temperature = 164° C., 1 atm, $H_2$ stream. Cat.: 120 ml of catalyst from Example 1.

| $H_2$/aniline mol/mol | Space velocity kg/l × h | ANI % | CHA % | DCA % | Anone + Anol % | LB % | UC % | Time of operation h |
|---|---|---|---|---|---|---|---|---|
| 40 | 0.22 | 0 | 97.8 | 1.9 | 0.24 | 0.06 | 0.03 | 18 |
| 40 | 0.22 | 0 | 98.3 | 1.5 | 0.13 | 0.09 | 0.02 | 133 |
| 40 | 0.22 | 0 | 98.3 | 1.4 | 0.24 | 0.08 | 0.06 | 314 |
| 40 | 0.22 | 0.17 | 98.1 | 1.5 | 0.12 | 0.06 | 0.03 | 475 |
| 40 | 0.22 | 0.17 | 97.2 | 2.0 | 0.47 | 0.05 | 0.02 | 1000 |
| 40 | 0.22 | 0.75 | 97.0 | 2.3 | 0.09 | 0 | 0.01 | 1583 |
| 43 | 0.20 | 0.95 | 96.6 | 2.4 | 0 | 0 | 0 | 2113 |

The catalyst is particularly suitable for industrial cyclohexylamine production because it can be regenerated by burning-off and reducing with hydrogen and renewed impregnation of the catalyst with dilute NaOH increases the selectivity for cyclohexylamine to above 99%!

Example 6 (Influence of ammonia with atmospheric pressure metering)

If five mol of ammonia per mole of aniline are mixed into the feed stream in the experiment from Example 5, the conversion of 100% quickly drops to about 80%. In this experiment, the selectivity was generally higher and rose from about 99.4% to about 99.7% as a result of the ammonia addition.

Example 7 (Influence of the hydrogen pressure)

The experiment of Example 5 was repeated in a pressure-resistant reaction tube, with both the pressure and the space velocity being increased in steps.

TABLE 5

Aniline hydrogenation, oil temperature = 164° C., $H_2$/aniline = 40/1.
Cat.: 120 ml of catalyst from Example 1.

| Pressure bar | Space velocity kg/l × h | ANI % | CHA % | DCA % | Anone + Anol % | Sel-UC % | Sel-ect. % | Time of operation h |
|---|---|---|---|---|---|---|---|---|
| 2 | 0.22 | 0 | 98.7 | 1.2 | 0 | 0.10 | 98.7 | 70 |
| 2 | 0.41 | 0 | 99.0 | 0.9 | 0.09 | 0.01 | 99.0 | 242 |
| 2 | 1.12 | 2.0 | 96.9 | 0.17 | 0.17 | 0 | 98.9 | 552 |
| 4 | 1.74 | 0 | 98.5 | 1.3 | 0.17 | 0.03 | 98.5 | 649 |
| 4 | 1.74 | 1.17 | 97.8 | 0.9 | 0.10 | 0.03 | 99.0 | 816 |
| 6 | 1.74 | 0 | 98.5 | 1.3 | 0.14 | 0.01 | 98.5 | 864 |
| 6 | 1.74 | 0.62 | 98.0 | 1.2 | 0.13 | 0.05 | 98.6 | 1200 |
| 6 | 1.74 | 0.46 | 98.4 | 1.1 | 0.12 | 0 | 98.9 | 1530 |

It can be seen that use of slight pressures enables the space velocity over the catalyst to be increased significantly without impairing the operating life of the catalyst or the selectivity of the process.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for hydrogenating aromatic amines into cycloaliphatic amines, at a pressure ranging from 0.5 to 40 bar, comprising hydrogenating an aromatic amine over a supported nobel metal catalyst which has been treated with bases, wherein the support of the supported noble metal catalyst has been treated with a salt component based on a metal comprising a member selected from the group consisting of chromium, molybdenum, tungsten, manganese, rhenium, and mixtures of the foregoing metals, and wherein the support is activated with rhodium.

2. The process of claim 1, wherein the salt component comprises a salt selected from the group consisting of chromium acetates, molybdenum acetates, tungsten acetates, manganese acetates, rhenium acetates, chromium nitrates, molybdenum nitrates, tungsten nitrates, manganese nitrates, rhenium nitrates, chromium halides, molybdenum halides, tungsten halides, manganese halides, rhenium halides, chromium sulphates, molybdenum sulphates, tungsten sulphates, manganese sulphates, rhenium sulphates, ammonium salts based on chromium oxides, ammonium salts based on molybdenum oxides, ammonium salts based on tungsten oxides, ammonium salts based on manganese oxides, ammonium salts based on rhenium oxides, and mixtures of these salts.

3. The process of claim 1, wherein in addition to being activated with rhodium, the support is activated with a noble metal comprising a component selected from the group consisting of iridium, ruthenium, osmium, palladium, and platinum.

4. The process of claim 1, wherein the supported noble metal catalyst used contains from 0.1 to 10% by weight of noble metal of which from 100 to 30% is rhodium.

5. The process of claim 1, wherein the supported noble metal catalyst contains from 0.05 to 5% by weight of a component selected from the group consisting of chromium, molybdenum, tungsten, manganese, rhenium, and mixtures thereof and also from 0.05 to 15% by weight of alkali metal or alkaline earth metal ions and, if desired, from 0.05 to 3% by weight of sulphur in the form of compounds.

6. The process of claim 1, wherein the process involves catalytic hydrogenation of an aromatic component comprising a component selected from the group consisting of aniline, $C_1$–$C_6$-alkylanilines alkylated either on the ring or on the nitrogen, $C_1$–$C_6$-alkylated diaminobenzenes, aminonaphthalenes and $C_1$–$C_3$-alkylated aminonaphthalenes, diaminonaphthalenes and diamino-diphenyl-$C_1$–$C_3$-alkanes.

7. The process of claim 1, wherein the process produces the cycloaliphatic amines with a selectivity that is greater than 90%.

8. The process of claim 1, wherein the process produces the cycloaliphatic amines with a selectivity that is greater than 95%.

9. The process of claim 1, wherein the process produces the cycloaliphatic amines with a selectivity that is about 100%.

10. A process for preparing a supported noble metal catalyst comprising:

(a) treating a support with a salt component and a hydroxide component, wherein the salt component comprises a component selected from the group consisting of chromium metal salts, molybdenum metal salts, tungsten metal salts, manganese metal salts and rhenium metal salts, chromium metal oxides, molybdenum metal oxide, tungsten metal oxides, manganese metal oxides and rhenium metal oxides, and mixtures thereof, with coprecipitation of oxide/hydroxide mixtures,
wherein the hydroxide component comprises a component selected from the group consisting of alkali metal hydroxides, alkaline earth metal hydroxides and ammonium hydroxides;

(b) drying and heating the support at a temperature ranging from 200 to 450° C., (c) treating the support with a component comprising an active substance selected from the group consisting of rhodium, iridium, ruthenium, osmium, palladium, platinum, alkali metal hydroxides, alkaline earth metal hydroxides, alkali metal sulphates, alkaline earth metal sulphates; and (d) drying and reducing with hydrogen at a temperature of from 80 to 350° C.

11. The process of claim 10, wherein soluble components are washed out with water at step (a).

12. The supported noble metal catalyst of claim 10, wherein the support comprises a component selected from the group consisting of aluminas, $Al_2O_3$ in its various modifications (α, κ, η, δ), supports customary for noble metals, e.g. $TiO_2$, kieselguhr, silica gel, $BaCO_3$, $CaCO_3$, ZnO, MgO, pumice, $ZrO_2$, activated carbon, chromium oxides, molybdenum oxides, tungsten oxides, manganese oxides and rhenium oxides, chromium hydrated oxides, molybdenum hydrated oxides, tungsten hydrated oxides, manganese hydrated oxides and rhenium hydrated oxides.

* * * * *